(12) United States Patent
Freedman et al.

(10) Patent No.: US 12,743,753 B1
(45) Date of Patent: Sep. 22, 2026

(54) MASKING MODEL FOR VISUALIZING UNCERTAINTY IN IMAGE-TO-IMAGE RECONSTRUCTION

(71) Applicant: Verily Health Inc., Dallas, TX (US)

(72) Inventors: Daniel Freedman, Zikhron Yaaqov (IL); Regev Cohen, Tel Aviv (IL); Gilad Kutiel, Zichron Yakov (IL); Michael Elad, Kiriat Tivon (IL)

(73) Assignee: Verily Health Inc., Dallas, TX (US)

( * ) Notice: Subject to any disclaimer, the term of this patent is extended or adjusted under 35 U.S.C. 154(b) by 260 days.

(21) Appl. No.: 18/462,122

(22) Filed: Sep. 6, 2023

Related U.S. Application Data

(60) Provisional application No. 63/482,660, filed on Feb. 1, 2023, provisional application No. 63/410,507, filed on Sep. 27, 2022.

(51) Int. Cl.

| | |
|---|---|
| ***G06T 3/4053*** | (2024.01) |
| ***G06T 3/4046*** | (2024.01) |
| ***G06T 5/77*** | (2024.01) |
| ***G06T 7/00*** | (2017.01) |
| ***G06T 11/10*** | (2026.01) |
| ***G16H 30/40*** | (2018.01) |

(52) U.S. Cl.
CPC .............. *G06T 5/77* (2024.01); *G06T 3/4046* (2013.01); *G06T 3/4053* (2013.01); *G06T 7/0012* (2013.01); *G06T 11/10* (2026.01); *G16H 30/40* (2018.01); *G06T 2207/20081* (2013.01); *G06T 2207/20084* (2013.01); *G06T 2207/30004* (2013.01); *G06T 2210/41* (2013.01)

(58) Field of Classification Search
CPC ....... G06T 5/77; G06T 3/4046; G06T 3/4053; G06T 7/0012; G06T 11/001; G06T 2207/20081; G06T 2207/20084; G06T 2207/30004; G06T 2210/41; G16H 30/40
See application file for complete search history.

(56) References Cited

U.S. PATENT DOCUMENTS 9,730,663 B2 * 8/2017 Koehler .................. G06T 7/149
10,878,219 B2 12/2020 Zhou et al.
(Continued)

FOREIGN PATENT DOCUMENTS

CN 110363047 B * 10/2021 ........... G06V 40/171

OTHER PUBLICATIONS

Angelopoulos et al. “Image-to-Image Regression with Distribution-Free Uncertainty Quantification and Applications in Imaging.” arXiv:2202.05265v1 [cs.LG] Feb. 10, 2022. (16 pgs).
(Continued)

*Primary Examiner* — John Villecco
*Assistant Examiner* — Kyla Guan-Ping Tiao Allen
(74) *Attorney, Agent, or Firm* — Christensen O’Connor Johnson Kindness PLLC

(57) ABSTRACT

Methods and systems of processing medical image data are presented herein. Some methods may include the steps of: receiving image data representing at least one medical image; generating a reconstructed image based on the image data; generating a mask from the image data and the reconstructed image using a pre-trained machine learning model; and applying the mask to the reconstructed image to generate a masked reconstructed image. The mask may include at least three uncertainty levels for a plurality of pixels in the reconstructed image.

20 Claims, 13 Drawing Sheets

(56) References Cited

U.S. PATENT DOCUMENTS

| | | | | |
|---|---|---|---|---|
| 2015/0317828 | A1* | 11/2015 | Isaksson | G06F 16/29<br>382/103 |
| 2019/0057488 | A1* | 2/2019 | Li | G06T 7/136 |
| 2019/0325620 | A1* | 10/2019 | Adler | G06T 7/10 |
| 2020/0302596 | A1* | 9/2020 | Yoo | G06T 7/11 |
| 2021/0264589 | A1 | 8/2021 | Jacob et al. | |
| 2023/0132180 | A1* | 4/2023 | Hsieh | G06T 7/11<br>382/299 |
| 2023/0230228 | A1* | 7/2023 | Liu | G06V 10/761 |
| 2023/0368913 | A1* | 11/2023 | Liu | G16H 30/40 |

OTHER PUBLICATIONS

Anonymous Authors, paper under double-blind review, What's Behind the Mask: Estimating Uncertainty in Image-to-Image Problems, Eleventh International Conference on Learning Representations 2023, https://openreview.net/pdf?id=kzqRIEHBgH, 24 pages.

* cited by examiner

MASKING MODEL FOR VISUALIZING UNCERTAINTY IN IMAGE-TO-IMAGE RECONSTRUCTION

CROSS-REFERENCE TO RELATED APPLICATIONS

The present application claims the benefit of U.S. Provisional Application No. 63/410,507, filed on Sep. 27, 2022, and U.S. Provisional Application No. 63/482,660, filed on Feb. 1, 2023, and both of these provisional applications are incorporated by reference herein in their entirety.

TECHNICAL FIELD

The present disclosure relates generally to image-to-image reconstruction and, in particular, visualizing the uncertainty of the image-to-image reconstruction process using masking.

BACKGROUND

Image-to-image reconstruction is the process of taking incomplete, damaged, or inaccurate image data and using mathematical algorithms to create the true image that the image data represents. Being able to reconstruct an image from deficient image data is important in many applications. For example, in biological or medical imaging, the image data collected may not be as robust as desired, so it may be advantageous to perform image-to-image reconstruction on the image data to generate a reconstructed image that is as close as possible to the true image.

However, image-to-image reconstruction may generate a reconstructed image that is different from the desired image. Thus, it is important to calculate and understand how similar the output image is to the true image, particularly in biological or medical imaging where fidelity to the true image is paramount. For these reasons, improved processes are needed to accurately calculate and conveniently display the uncertainty associated with the reconstructed image generated by image-to-image reconstruction.

SUMMARY

Methods of processing medical image data using a processor are presented herein. Some methods may include the steps of: receiving image data representing at least one medical image; generating a reconstructed image based on the image data; generating a mask from the image data and the reconstructed image using a pre-trained machine learning model; and applying the mask to the reconstructed image to generate a masked reconstructed image. The mask may include at least three uncertainty levels for a plurality of pixels in the reconstructed image.

In some embodiments, each of the at least three uncertainty levels may be a value in a range of 0 to 1. In some embodiments, generating the reconstructed image may include colorization of the image data. In some embodiments, generating the reconstructed image may include identifying and estimating missing parts of the received image data. In some embodiments, the image data may represent an image of a first resolution and the reconstructed image may represent an image of a second resolution, where the second resolution is higher than the first resolution. In some embodiments, receiving the image data may include collecting the image data from a medical device. The medical device may be at least one of: an endoscope, a magnetic resonance imaging device, ultrasound device, X-ray device, or any other suitable medical device for capturing medical images. In some embodiments, the pre-trained machine learning model may be trained on a series of images to generate a mask for each image such that the distance between each masked reconstructed image and a corresponding true image is less than a first threshold with probability greater than a second threshold. In some embodiments, the mask may represent a visual representation of confidence that portions of the reconstructed image are accurate. In some embodiments, the method may also include displaying the mask and the masked reconstructed image on a display.

Systems for processing medical image data are described herein. In some embodiments, the system may include an input interface configured to receive image data representing at least one medical image, a memory configured to store a plurality of processor-executable instructions, and a processor configured to execute the plurality of processor-executable instructions to perform operations. The memory may include an image-to-image model and a masking model, where the masking model includes a pre-trained machine learning model. The operations performed may include: receiving image data; generating a reconstructed image based on the image data using the image-to-image model; generating a mask from the image data and the reconstructed image using the masking model, wherein the mask comprises at least three uncertainty levels for a plurality of pixels in the reconstructed image; and generating a masked reconstructed image based on the reconstructed image and the mask.

In some embodiments, each of the at least three uncertainty levels may be a value in a range of 0 to 1. In some embodiments, the pre-trained machine learning model may be trained on a series of images to generate a mask for each image such that the distance between each masked reconstructed image and a corresponding true image is less than a first threshold with probability greater than a second threshold. In some embodiments, the mask may represent a visual representation of confidence that portions of the reconstructed image are accurate. In some embodiments, the operations performed may also include displaying the mask and the masked reconstructed image on a display.

Non-transitory processor-readable storage mediums storing a plurality of processor-executable instructions for processing medical image data are described herein. The instructions executed by the processor may perform operations including: receiving image data representing at least one medical image; generating a reconstructed image based on the image data; generating a mask from the image data and the reconstructed image using a pre-trained machine learning model, wherein the mask comprises at least three uncertainty levels for a plurality of pixels in the reconstructed image; and generating a masked reconstructed image based on the reconstructed image and the mask.

In some embodiments, each of the at least three uncertainty levels may be a value in a range of 0 to 1. In some embodiments, the pre-trained machine learning model may be trained on a series of images to generate a mask for each image such that the distance between each masked reconstructed image and a corresponding true image is less than a first threshold with probability greater than a second threshold. In some embodiments, the mask may represent a visual representation of confidence that portions of the reconstructed image are accurate. In some embodiments, the operations performed may also include displaying the mask and the masked reconstructed image on a display.

BRIEF DESCRIPTION OF THE DRAWINGS

Illustrative embodiments of the present disclosure will be described with reference to the accompanying drawings, of which.

DETAILED DESCRIPTION

Figure 1:
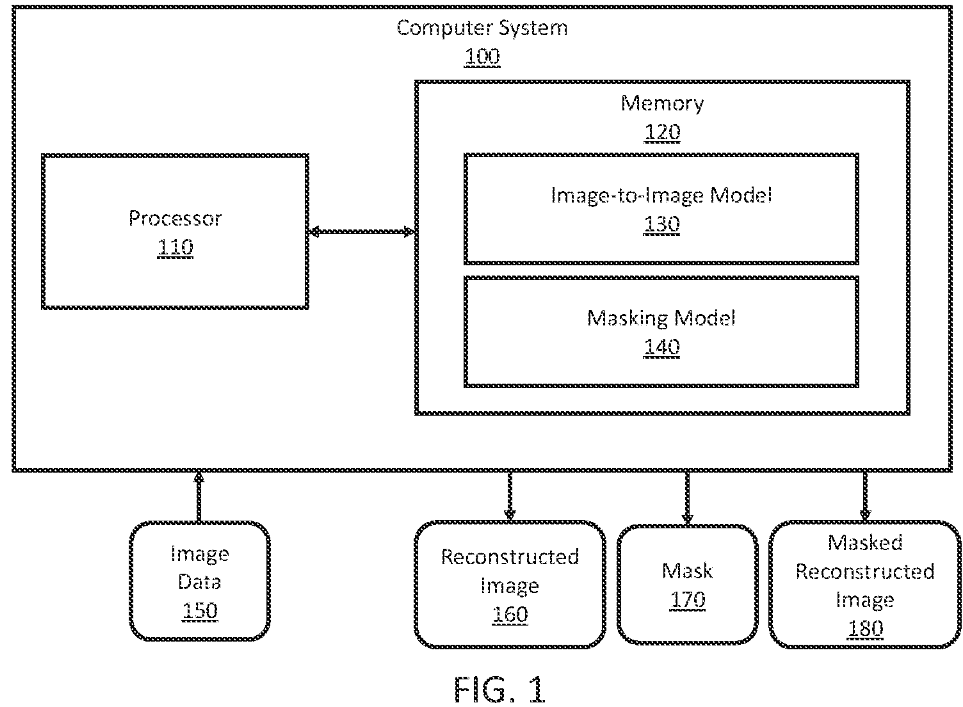
FIG. 1 is a simplified diagram of a computing device for implementing an example image-to-image model and masking model, according to one or more embodiments described herein.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, the term "network" may comprise any hardware or software-based framework that includes any artificial intelligence network or system, neural network or system and/or any training or learning models implemented thereon or therewith.

As used herein, the term "model" may comprise hardware or software-based framework that performs one or more functions. In some embodiments, the module may be implemented on one or more neural networks.

Image-to-image reconstruction may be used in various applications to reconstruct the true image from damaged, incomplete, or inaccurate image data. Image-to-image reconstruction may leverage the power of machine learning, specifically neural networks, to predict the true image using the image data. Although the reconstructed images generated by image-to-image reconstruction may approach high fidelity to the true image, the reconstructed image sometimes does not match the true image exactly. Thus, understanding how similar the reconstructed image is to the true image is vital to determining how much to rely on the reconstructed image.

This may be especially important for biological or medical images. For example, a physician may use medical images collected from colonoscopy videos or MRI devices to diagnose diseases or injuries. In some cases, the medical images collected may approximate the true images of the patient's body. For example, the medical image may have low resolution or may be missing one or more parts. Thus, image-to-image reconstruction may be used to reconstruct the true image of the patient's body, which may be more helpful to the physician. However, there may be uncertainty associated with how closely the reconstructed image matches the true image. Therefore, a physician viewing the reconstructed image needs to be able to understand the uncertainty associated with it to properly rely on the image when treating patients.

As a result, it is important to develop a process for accurately calculating and conveying the uncertainty associated with one or more parts of a reconstructed image. As described herein, the present disclosure relates to a masking model that can be used with any image-to-image model. The masking model may calculate the value of the uncertainty for each pixel of the reconstructed image. The uncertainty value may then be used to determine the size of the mask that is needed at each pixel. For example, a continuous mask may be used which includes a gradient of mask sizes between 0 and 1 rather than a simple, conventional binary mask value that either does not mask a pixel (one value) or completely blocks the pixel (the second value). The mask can then be combined with the reconstructed image to convey the uncertainty associated with each pixel of the reconstructed image at a more granular level.

These descriptions are provided for example purposes only and should not be considered to limit the scope of the invention described herein. Certain features may be added, removed, or modified without departing from the spirit of the claimed subject matter.

FIG. 1 is a schematic diagram illustrating a computer system 100 for implementing an image-to-image model 130 and a masking model 140, according to some embodiments of the present disclosure. The computer system 100 includes a processor 110 coupled to a memory 120. Although the computing device 100 is shown with only one processor 110, it is understood that processor 110 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in the computing device 100. The computing device 100 may be implemented as a stand-alone subsystem, as a board added to a computing device, and/or as a virtual machine. The memory 120 may be used to store software executed by computing device 100 and/or one or more data structures used during operation of computing device 100. The memory 120 may include one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor (e.g., the processor 110) or computer is adapted to read. In the present embodiments, for example, the memory 120 includes instructions suitable for training and/or using an image-to-image model 130 and/or a masking model 140 described herein.

The processor 110 and/or the memory 120 may be arranged in any suitable physical arrangement. In some embodiments, the processor 110 and/or the memory 120 are implemented on the same board, in the same package (e.g., system-in-package), on the same chip (e.g., system-on-chip), and/or the like. In some embodiments, the processor 110 and/or the memory 120 include distributed, virtualized, and/or containerized computing resources. Consistent with such embodiments, the processor 110 and/or the memory 120 may be located in one or more data centers and/or cloud computing facilities.

In some examples, the memory 120 may include non-transitory, tangible, machine readable media that includes executable code that when run by one or more processors (e.g., the processor 110) may cause the one or more processors to perform the methods described in further detail herein. For example, as shown, the memory 120 includes instructions for an image-to-image model 130 and a masking model 140 that may be used to implement and/or emulate the systems and models, and/or to implement any of the methods described further herein. In some embodiments, the image-to-image model 130 may receive image data 150 and generate a reconstructed image 160. The masking model 140 may use the image data 150 and the reconstructed image 160 to generate a mask 170 for the image representing the uncertainty associated with the reconstructed image at one or more pixels. The memory 120 may also include instructions for combining the reconstructed image 160 and the mask 170 to generate a masked reconstructed image 180 that visually conveys the uncertainty associated with the reconstructed image 170.

In this disclosure, any operation between a vector and a scalar is represented as the element wise operation, for example, $2+[1; 2; 3]=[3; 4; 5]$. The $\odot$ operator is used to denote element-wise multiplication between vectors, i.e., $[1,2,3]\odot[4,5,6]=[4,10,18]$. Moreover, a mask $m\in[0,1]^n$ may be an n-dimensional vector. Thus, m may mask y if y is multiplied element-wise with m as shown by: ym. In this disclosure, the size of a mask may be equal to $1-\|m\|_1$. As a result, the mask $\vec{1}$ has a size 0 and the mask $\vec{0}$ has a size 1. Additionally, $d(*,*)$ may denote a general distortion measure between two images and, when subscripted with m, $d_m(y,\hat{y})=d(ym,\hat{y}\ m)$ $d_m(y,\hat{y})=d(y\odot m,\hat{y}\odot m)$.

Figure 2:
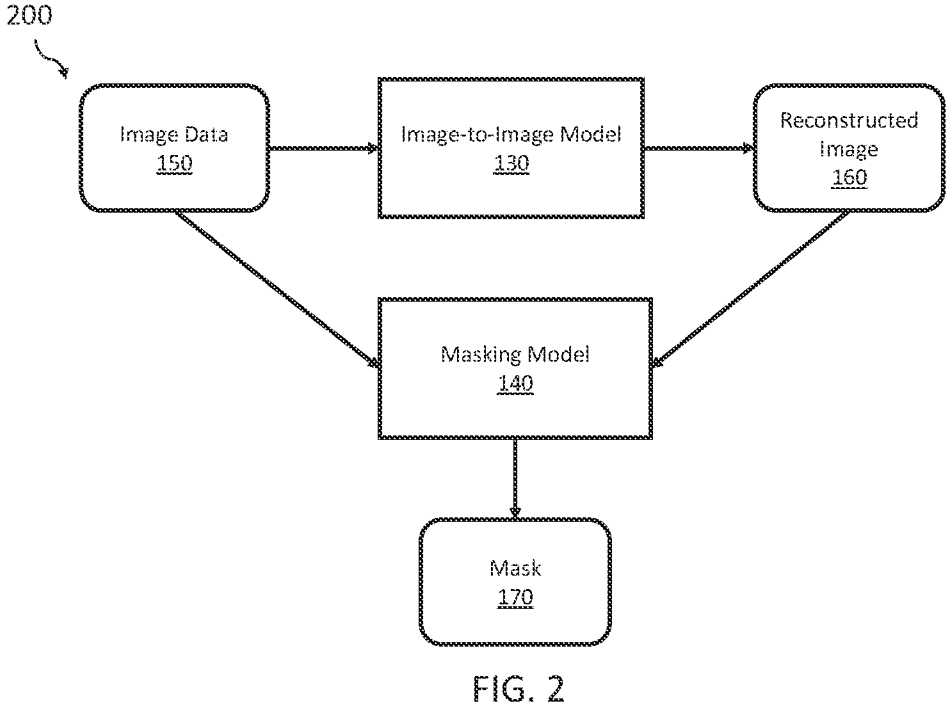
FIG. 2 is a simplified diagram illustrating an example embodiment of a process of generating a reconstructed image and mask, according to one or more embodiments described herein.

FIG. 2 is a simplified diagram illustrating the process 200 of generating a reconstructed image 160 and a mask 170 using the image-to-image model 130 and the masking model 140, respectively, according to some embodiments of the present disclosure. The image-to-image model 130 and the masking model 140 used to generate the reconstructed image 160, the mask 170, and the masked reconstructed image 180 from the image data 150 may be described in "What's Behind the Mask: Estimating Uncertainty in Image-to-Image Problems," submitted to the Eleventh International Conference on Learning Representations, the entirety of which is incorporated herein by reference.

The image-to-image model 130 may be any suitable image-to-image model 130. In one example, the image-to-image model 130 may perform image colorization. The image colorization model may receive image data 150 with degraded, incomplete, or inaccurate coloring or a gray-scale image and reconstruct the color of the image data 150 to estimate the color of the desired or true image. In another example, the image-to-image model 130 may perform image completion. The image completion model may receive image data 150 that is incomplete or is missing parts of the true image. The image completion model may then reconstruct the incomplete or missing parts. In yet another example, the image-to-image model 130 may perform super resolution. The super resolution model may receive image data 150 that has a low resolution and generate a reconstructed image 160 with a higher resolution than the image data 150. Although several examples of image-to-image models 130 have been described, it is contemplated that any suitable image-to-image model 130 may be used including, for example, deblurring or denoising.

In some embodiments, the image-to-image model 130 may include a machine learning model or, in particular, a neural network. The neural network of the image-to-image model 130 may be trained in any suitable way. For example, the neural network may be trained by inputting image data 150 that is incomplete, degraded, or inaccurate and outputting a reconstructed image 160. The reconstructed image 160 may then be compared to the desired or true image that the input image data 150 corresponds to. The neural network may be trained so that it generates reconstructed images 160 that are as close to the true image as possible. Embodiments of the training process are described in more detail below in relation to FIG. 12.

Although the trained neural network attempts to reproduce the true image, the reconstructed images 160 generated by the image-to-image model 130 may be different than the true image. In some cases, the size of the difference between the reconstructed image 160 and the true image (or the distance between the corresponding pixels of the true image) may vary across the reconstructed image 160. In other words, certain parts of the reconstructed image 160 may have a larger difference from the corresponding part on the true image than the difference for other parts of the reconstructed image 160. Thus, there may be an uncertainty associated with various parts of the reconstructed image 160. In some cases, there may be a different uncertainty associated with each pixel of the reconstructed image 160.

The masking model 140 may estimate the uncertainty associated with each part or pixel of the reconstructed image 160 and generate a mask 170 representing the uncertainty at each part or pixel. The masking model 140 may receive the image data 150 and the reconstructed image 160 and use them to generate a mask 170.

Any suitable masking model 140 may be used. In some embodiments, the masking model 140 may include a machine learning model and, in particular, a neural network. For example, the neural network may be an 8-layer U-Net such as a regressor or a conditional generator with an adversarial discriminator (GAD).

The true image y may be represented as $y\in[0,1]n$ and the image data corresponding to y may be represented as $x\in[0,1]^{n_x}$. The reconstructed image f may be represented as $\hat{y}\in[0,1]n$. Thus, the uncertainty U(x) of ŷ given x may be calculated using Equation 1 below:

$$U(x) = \mathop{\mathbb{E}}_{y|x,\hat{y}|x}[d(y, \hat{y})] \tag{1}$$

where d(y,ŷ) may denote an arbitrary distortion measure between the true image y and the reconstructed image ŷ. The reconstructed image ŷ may be chosen to satisfy Equation 2 below:

$$P(U(x) \le \alpha) \ge \beta \tag{2}$$

where α is greater than or equal to 0 and β is in a range of 0 to 1. In some embodiments, α and β may be chosen by a user. In some cases, Equation 2 above may be an ideal scenario and may not always be satisfied in practice. Instead, the mask 170 represented by $m\in[0,1]^n$ may be generated according to Equation 3 below:

$$P\left(\mathop{\mathbb{E}}_{y|x,\hat{y}|x}[d_m(y, \hat{y})] \le \alpha\right) \ge \beta \tag{3}$$

where $d_m(y, \hat{y}) \triangleq (m\cdot y, m\cdot\hat{y})$.

When the masking model 140 includes a neural network, the masking model may be represented by $m_\theta(x, \hat{y}) \triangleq N(x, \hat{y}; \theta)$ where θ is a parameter. The masking model 140 may be optimized according to the loss function represented by Equation 4 below:

$$\ell(\mathcal{D}, \theta) = \sum_{(x,\hat{y},y)\in\mathcal{D}} \left\| m_\theta(x, \hat{y}) - \vec{1} \right\|_2^2 + \mu d_{m_\theta}(y, \hat{y}) \tag{4}$$

where D may be a dataset including the image data 150 (x), the reconstructed image 160 (ŷ), and the true image (y) and may be represented by $D\triangleq\{x, \hat{y}, y\}$.

In some embodiments, the masking model 140 may be trained using the image data 150, the reconstructed image 160, and the true image. The masking model 140 may receive the image data 150 and the reconstructed image 160 and may generate a mask 170 based on the image data 150 and the reconstructed image 160. The true image may then be used to determine the loss according to Equation 4 above. The masking model 140 may then be optimized to minimize the loss associated with the generating the mask 170. The training process is described in more detail below in reference to FIG. 12.

In some embodiments, the uncertainty value determined by the masking model 140 may be further calibrated to obtain stronger statistical guarantees. The masking model 140 may be calibrated in any suitable way. For example, each entry mi of the mask may be multiplied by $$\frac{\lambda}{m_i(1-m_i)},$$

where λ may be a global scalar calculated by the calibration procedure. Given a calibration dataset of triples $C=\{(x_i, \hat{y}_i, y_i)\}$, $\{\lambda_i\}$ may be calculated using Algorithm 1 below:

Algorithm 1 Finding $\lambda_i$

```
def scale (lambda_, mask, eps=1e-6):
  return (mask * lambda_ / (eps + mask * (1 - mask))),clip (0, 1)
def find_lambda(mask, y, y_hat, eps=1e-4):
  l, h, lambda_ = eps, 1 / eps, 0
  while h - l > eps:
    lambda_ = (h + l) / 2
    loss = loss_fn(
      y * scale(a, mask),
      y_hat * scale(a, mask))
    if loss > alpha:
      h = a
    else:
      l = a
  return lambda_
```

Where λ may be set to be in the 1−β quantile of $\{\lambda_i\}$ or, in other words, the maximal value for which at least β fraction of the calibration sets satisfies condition (P1). Thus, the final mask, calibrated according to α and β, may be guaranteed to satisfy condition (P1) with probability at least β. As a result, the training process can accept any distortion measure and the model is trained only once, irrespective of α and β. The calibration process may be easily adapted for different values of α and β.

Figure 3:
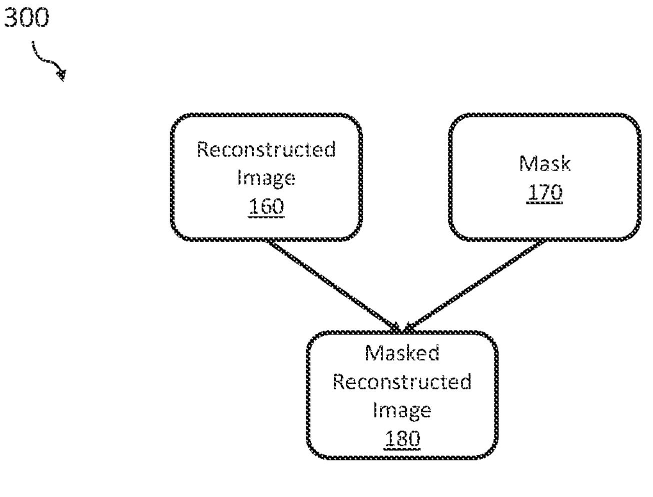
FIG. 3 is a simplified diagram illustrating an example embodiment of a process of generating a masked reconstructed image, according to one or more embodiments described herein.

FIG. 3 is a simplified diagram illustrating the process 300 of generating a masked reconstructed image 180, according to some embodiments of the present disclosure. The masked reconstructed image 180 may be generated based on the mask 170 and the reconstructed image 160. The mask 170 may be combined with the reconstructed image 160 in any suitable way. For example, the mask 170 and the reconstructed image 160 may be represented by an n-dimensional vector. The vectors representing the mask 170 and the reconstructed image 160 may be multiplied element-wise such that each element n of the mask 170 may be multiplied by the corresponding element n of the reconstructed image 170. Thus, the resulting n-dimensional vector may correspond to the masked reconstructed image 180. The elements n of the vectors may correspond to a single pixel or multiple pixels of the image.

In some embodiments, the mask 170 generated by the masking model 140 may be a binary mask, in which, for each pixel of the reconstructed image 160, one value is assigned to the corresponding pixel in the mask 170 if the uncertainty exceeds a certain threshold or a second value is assigned if the uncertainty does not exceed a certain threshold. However, it may be desirable to generate a mask 170 that uses more than two values that correspond to the uncertainty. For example, each element of the mask 170 may fall within an effectively continuous range of values between, and including, 0 and 1. The mask values may be quantized for implementation on a computer. For example, the values may be one of 4, 8, 16, 32, or 64 values in the range of [0,1] or one of any number of values greater than two (i.e., a binary mask) that is a power of two. Because the uncertainty may vary across the reconstructed image 160, a continuous mask may provide more information about the actual level of uncertainty at each pixel.

In some embodiments, the uncertainty value assigned to each pixel in the mask 170 may be a value between 0 and 1. The size of the mask at each pixel may be equal to one minus the uncertainty value. Thus, the size of a mask that has an uncertainty of 0 is 1 and the size of a mask that has an uncertainty of 1 is 0. Thus, if a pixel of the mask 170 has a size of 0, the reconstructed image 170 may not be masked at that pixel. On the other hand, if a pixel of the mask 170 has a size of 1, the reconstructed image may be completely masked at that pixel. For values between 0 and 1, the mask 170 will partially mask the corresponding pixel of the reconstructed image 160. There may be a gradient between 0 and 1 such that the pixel is masked more as the uncertainty value increases from 0 to 1.

Thus, the level of masking for each pixel of the reconstructed image 180 may visually convey the amount of uncertainty associated with that pixel. Pixels with less masking may represent values with a higher degree of confidence than pixels with more masking.

Generating the masked reconstructed image may be performed within either the image-to-image model 130 or the masking model 140 or another model or module that applies the mask to a reconstructed image.

Generating a reconstructed image 160, a mask 170, and a masked reconstructed image 180 using the disclosed processes, structures, and methods provide several benefits. For example, the disclosed masking model 140 may be used with any image-to-image model 130. The masking model 140 may be trained with any image-to-image model 130 and does not rely on the structure or function of the image-to-image model 130 to generate a mask 170 for the reconstructed image. Additionally, the mask 170 may be applied to any distance between the true image and the reconstructed image 160. The distance between each part or pixel of the true image and the masked reconstructed image 180 may be relatively small such that the distance is lower than a particular distance threshold. The probability that the distance between the true image and the masked reconstructed image 180 may be relatively high such that the probability is higher than a particular uncertainty threshold.

Figure 4:
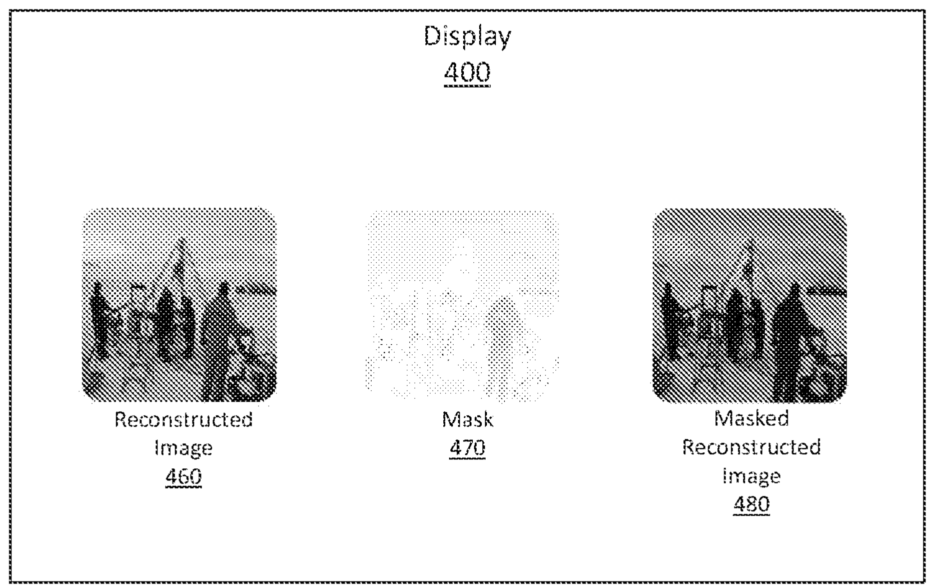
FIG. 4 is a simplified diagram illustrating a display, according to one or more embodiments described herein.

FIG. 4 is a simplified diagram illustrating a display, according to some embodiments of the present disclosure. Display 400 may be, for example, a liquid crystal display (LCD), a light-emitting diode (LED), a thin-film transistor (TFT) LCD, a backlit LCD, or a quantum dot LED (QLED), or any other suitable display. The display 400 may be a touchscreen. Moreover, the display 400 may be coupled to a computer system, such as computer system 100 illustrated in FIG. 1, via any wired or wireless connection, such as via a directly wired cable, via the Internet, or via a WiFi or other wireless network. A medical device that generates the image data 150 may likewise be connected to the computer system 100 via any wired or wireless connection. The devices may be remote from each other (e.g., connected via Internet) or located together in a room where medical procedures are performed.

In some embodiments, one or more of the reconstructed image 460 generated by the image-to-image model 130, the mask 470 generated by the masking model 140, and the masked reconstructed image 480 based on the mask 470 and reconstructed image 460 may be output on the display 400. In some cases, only the masked reconstructed image 480 may be output on the display 400. In other cases, the masked reconstructed image 480 may be output alongside the reconstructed image 460 or the mask 470. The reconstructed image 460, the mask 470, and/or the masked reconstructed image 480 may be arranged in any appropriate arrangement on the display 400 such as, for example, side-by-side.

The reconstructed image 460 in FIG. 4 is an example of a reconstructed image 160 according to one or more embodiments. Similarly, the mask 470 in FIG. 4 is an example of a mask 470 according to one or more embodiments. Moreover, the masked reconstructed image 480 in FIG. 4 is an example of a masked reconstructed image 180 according to one or more embodiments. The mask 470 may illustrate the uncertainty at different pixels of the reconstructed image 460. In this case, the darker parts of the mask 470 correspond to a higher uncertainty and the lighter parts correspond to a lower uncertainty. Thus, the darker parts of the marked reconstructed image 480 may be less reliable than the lighter parts.

Figure 5A:
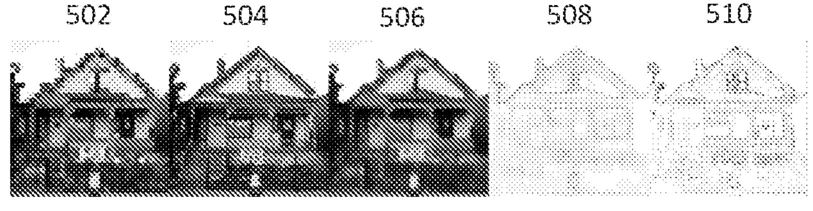
FIG. 5A is an example of several variations of an image, according to one or more embodiments described herein.

FIG. 5A is an example of several images produced during the processes of generating a reconstructed image 160 and a mask 170 as illustrated and described in reference to FIGS. 2-3. The image-to-image model 130 used to generate the images in FIG. 5A may include super resolution and the masking model 140 may be any suitable masking model described herein. The images in FIG. 5A represent a house, where image 504 is the true image. Image 502 may be a low-resolution image of the true image 504. In some cases, the image data 150 that is input into the image-to-image model 130 may include the low-resolution image 502. Image 506 may be the reconstructed image generated by the image-to-image model 130 based on the low-resolution image 502. The reconstructed image 506 may be at a higher resolution than the low-resolution image 502 input into the image-to-image model 130. Image 508 may be a mask generated by the masking model 140 that comprises a value of the uncertainty at each pixel. In the illustrated embodiment, the uncertainty level is continuous such that the pixels may be any value in a range of 0 to 1. The darker parts of the mask 508 correspond to more uncertainty and the lighter parts of the mask 508 correspond to less uncertainty. Thus, in the illustrated example, the uncertainty is higher along the edges of the house and, in particular, along the roof, for example. Image 510 is the absolute error between the reconstructed image 506 and the true image 504. In some embodiments, it may be desirable for the mask 508 to be as close to the absolute error 510 as possible given that the mask 508 generated during inference is not based on the true image 504. The absolute error 510 may be used during training to optimize the masking model 140.

Figure 5B:
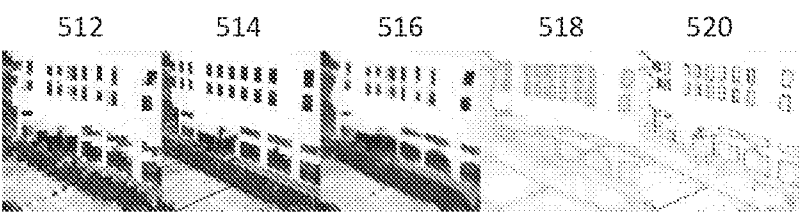
FIG. 5B is an example of several variations of an image, according to one or more embodiments described herein.

Similar to FIG. 5A, FIG. 5B is another example of several images produced during the processes of generating a reconstructed image 160 and a mask 170 as illustrated and described in reference to FIGS. 2-3. The image-to-image model 130 used to generate the images in FIG. 5B may include super resolution and the masking model 140 may be any suitable masking model described herein. The images in FIG. 5B represent a building, where image 514 is the true image. Image 512 may be a low-resolution image of the true image 514. In some cases, the image data 150 that is input into the image-to-image model 130 may include the low-resolution image 512. Image 516 may be the reconstructed image generated by the image-to-image model 130 based on the low-resolution image 512. The reconstructed image 516 may be at a higher resolution than the low-resolution image 512 input into the image-to-image model 130. Image 518 is a mask generated by the masking model 140 that comprises a value of the uncertainty at each pixel. In the illustrated embodiment, the uncertainty level is continuous such that the pixels may be any value in a range of 0 to 1. The darker parts of the mask 518 correspond to more uncertainty and the lighter parts of the mask 518 correspond to less uncertainty. Thus, in the illustrated example, the uncertainty is higher around the edges between different parts of the image and, in particular, along the windows and doors of the building, for example. Image 520 is the absolute error between the reconstructed image 516 and the true image 514. In some embodiments, it may be desirable for the mask 518 to be as close to the absolute error 520 as possible given that the mask 518 generated during inference is not based on the true image 514. The absolute error 520 may be used during training to optimize the masking model 140.

Experiment 1

Figure 6:
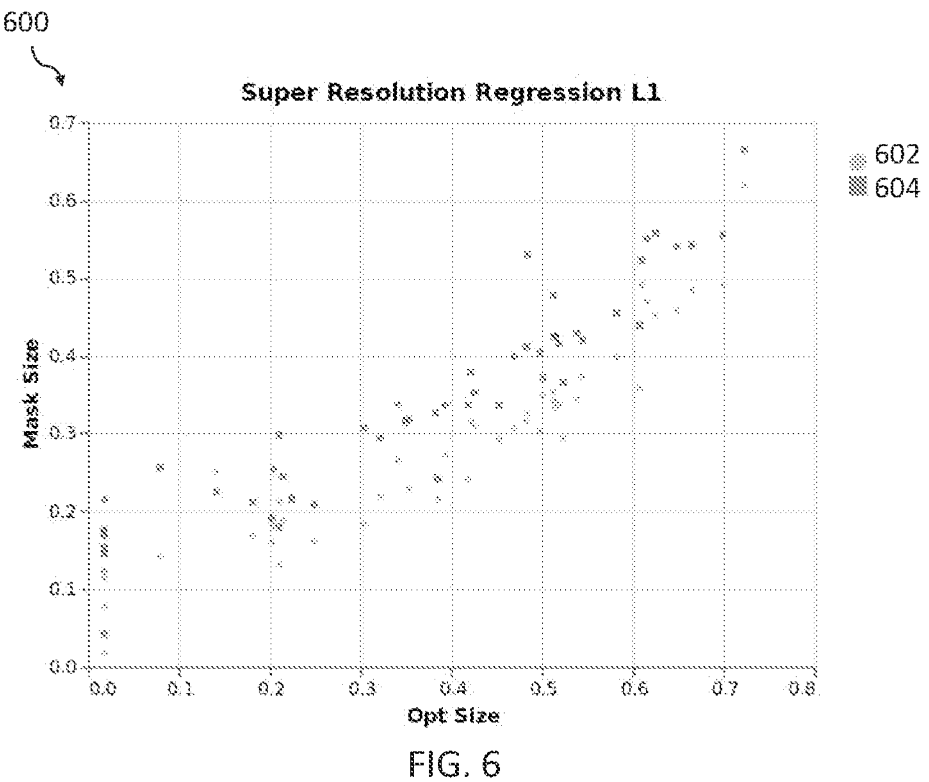
FIG. 6 is a plot illustrating the correlation between the size of various masks generated according to one example embodiment of the present disclosure.
Figure 7:
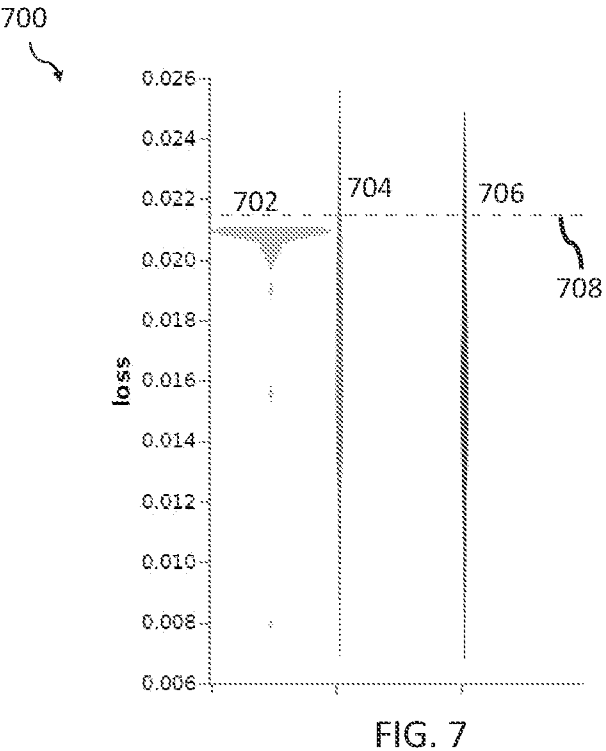
FIG. 7 is a plot illustrating the mask size distribution for various masks generated according to one example embodiment of the present disclosure.

FIGS. 6-7 are plots illustrating experimental results from a masking model applied to a regressor image-to-image model for the task of super resolution, according to some embodiments of the present disclosure. The image-to-image model used in Experiment 1 is a regression convolutional neural network with an 8 layer U-Net architecture, which herein may be referred to as a regressor. The regressor is designed to perform super resolution. During training, the regressor is optimized to minimize L1 loss, also known as the mean absolute error (MAE) or absolute error loss. The regressor is trained for two epochs using the Adam optimizer with a learning rate equal to 1e−5 and a batch size equal to 50.

The masking model used in Experiment 1 an 8-layer U-Net architecture as well. The masking model is also trained to minimize loss, which may be calculated according to Equation 4 above. For the purposes of discussing Experiment 1, the masking model used in this experiment, and exemplifying an embodiment according to the present disclosure, will be referred to as the disclosed masking model (which generates the disclosed mask).

The performance of the disclosed mask generated by the disclosed masking model is compared to a mask produced by quantile regression (a quantile mask), in which the uncertainty is estimated by bounding the value of each pixel with a confidence interval and by using a calibration procedure to guarantee that the value is within the confidence interval, as described in more detail in Anastasios N Angelopoulous, et al., *Image-to-image regression with distribution-free uncertainty quantification and applications in imaging*, arXiv, arXiv:2202.05265, 2022 (hereinafter "Angelpoulous"), the entirety of which is incorporated by reference. Moreover, the performance of the disclosed mask is also compared to an optimal mask generated using an oracle model optimized using a true image and a reconstructed image.

FIG. 6 is a plot 600 of the mask size compared to the size of the optimal mask for the disclosed mask 602 and the quantile mask 604. As shown, there is a higher correlation between the disclosed mask 602 and the optimal mask than the correlation between the quantile mask 604 and the optimal mask.

FIG. 7 is a plot 700 of the mask size distribution for the optimal mask 702, the disclosed mask 704, and the quantile mask 706. As illustrated, the disclosed mask 704 has a relatively low distribution compared to the quantile mask 706 and is closer to the threshold loss 708. The distribution of the disclosed mask 704 is also closer to and more similar to the distribution of the optimal mask 702 than the distribution of the quantile mask 706 is to the optimal mask 702.

Experiment 2

Figure 8:
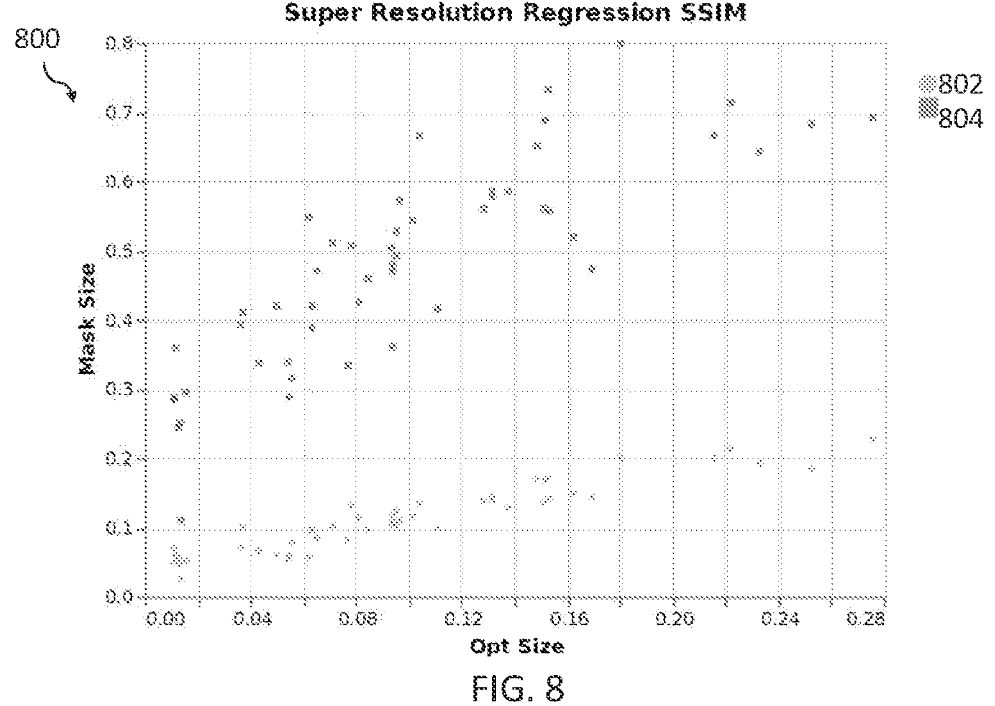
FIG. 8 is a plot illustrating the correlation between the size of various masks generated according to one example embodiment of the present disclosure.
Figure 9:
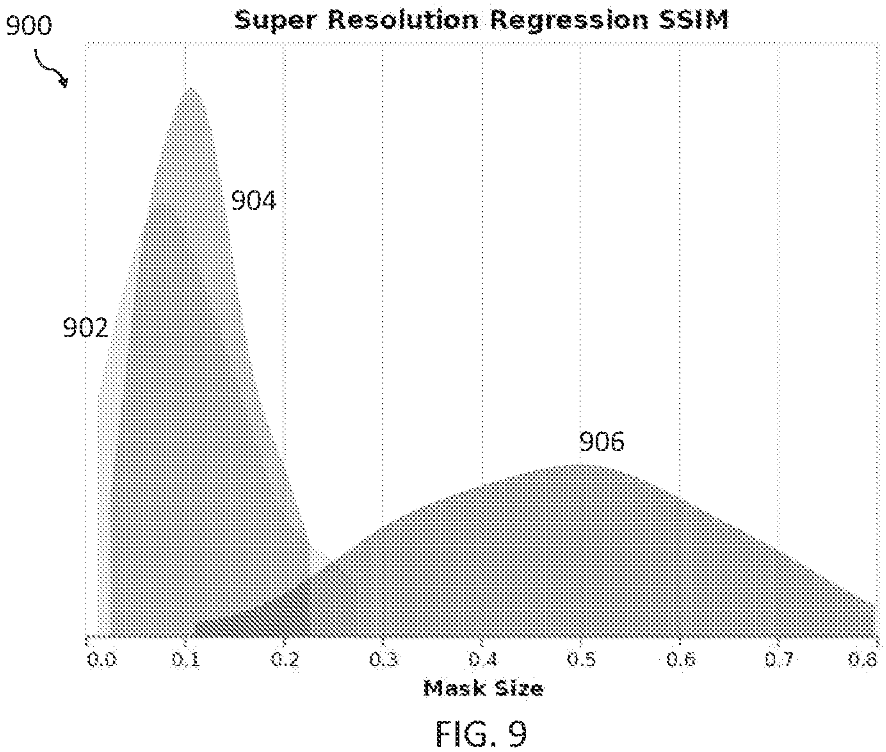
FIG. 9 is a plot illustrating the mask size distribution for various masks generated according to one example embodiment of the present disclosure.

FIGS. 8-9 are plots illustrating experimental results from a masking model applied to a regressor image-to-image model for the task of super resolution, according to some embodiments of the present disclosure. The image-to-image model used in Experiment 2 is a regression convolutional neural network with an 8 layer U-Net architecture, which herein may be referred to as a regressor. The regressor is designed to perform super resolution. Unlike the regressor model used in Experiment 1 and described in reference to FIGS. 6-7, the regressor used in Experiment 2 is trained to optimize the structural similarity index measure (SSIM), which is a method for measuring the similarity between two images. The regressor is trained for two epochs using the Adam optimizer with a learning rate equal to 1e−5 and a batch size equal to 50.

The masking model used in Experiment 2 is an 8-layer U-Net architecture as well. The masking model is trained to minimize loss, which may be calculated according to Equation 4 above. For the purposes of discussing Experiment 2, the masking model used in this experiment, and exemplifying an embodiment according to the present disclosure, will be referred to as the disclosed masking model (which generates the disclosed mask).

The performance of the disclosed mask generated by the disclosed masking model is compared to a mask produced by quantile regression (a quantile mask), in which the uncertainty is estimated by bounding the value of each pixel with a confidence interval and by using a calibration procedure to guarantee that the value is within the confidence interval, as described in Angelopoulous. Moreover, the performance of the disclosed mask is also compared to an optimal mask generated using an oracle model optimized using a true image and a reconstructed image.

FIG. 8 is a plot 800 of the mask size compared to the size of the optimal mask for the disclosed mask 802 and the quantile mask 804. As shown, there is a higher correlation between the disclosed mask 802 and the optimal mask than between the quantile mask 804 and the optimal mask.

FIG. 9 is a plot 900 of the mask size distribution for the optimal mask 902, the disclosed mask 904, and the quantile mask 906. As illustrated, the disclosed mask 904 has a relatively low distribution compared to the quantile mask 906. Moreover, the distribution of the disclosed mask 904 is closer to the distribution of the optimal mask 902 than the distribution of the quantile mask 906 is to the optimal mask 902.

Experiment 3

Figure 10:
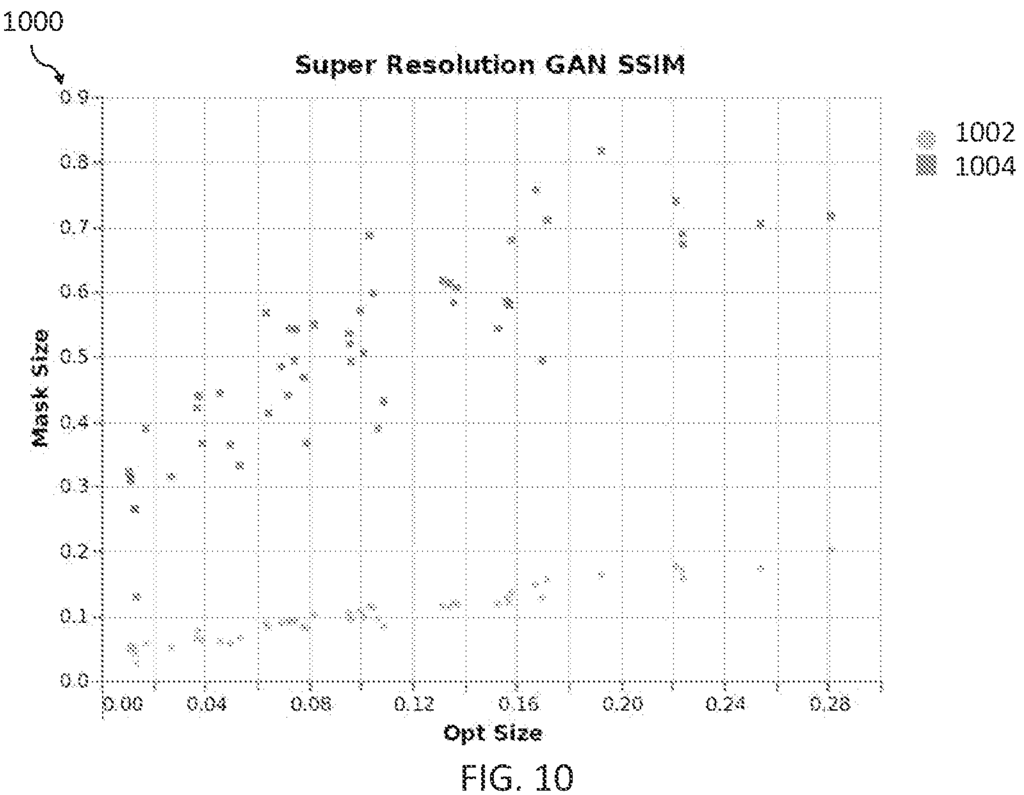
FIG. 10 is a plot illustrating the correlation between the size of various masks generated according to one example embodiment of the present disclosure.
Figure 11:
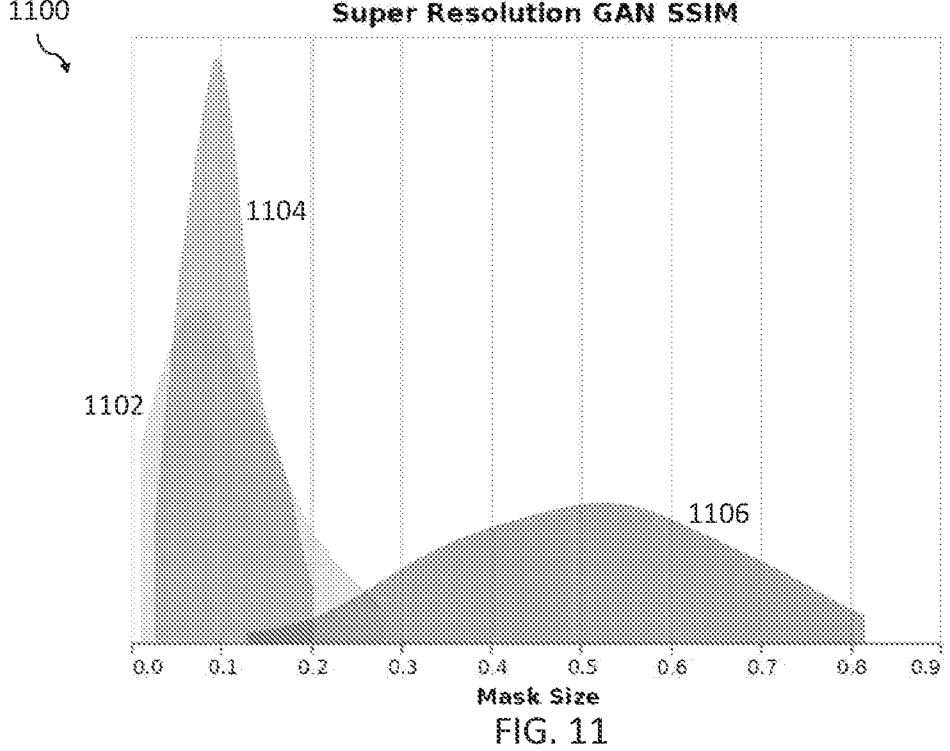
FIG. 11 is a plot illustrating the mask size distribution for various masks generated according to one example embodiment of the present disclosure.

FIGS. 10-11 are plots illustrating experimental results from a masking model applied to a GAN image-to-image model for the task of super resolution, according to some embodiments of the present disclosure. The image-to-image model used in Experiment 3 is a conditional GAN combined with an 8 layer U-Net architecture, which herein may be referred to as a GAN. The GAN is designed to perform super resolution. The discriminator of the GAN is a 4 layer convolutional neural network with a fully connected head.

GAN is trained to optimize the SSIM and the loss represented by Equation 5 below:

$$\mathcal{L}_{cGAN}(G, D) = \mathbb{E}_{x,y}[\log D(x, y)] + \mathbb{E}[\log(1 - d(x, G(x, y)))] \quad (5)$$

where λ is equal to 20. The GAN is trained for two epochs using the Adam optimizer with a learning rate equal to 1e−5 and a batch size equal to 50.

The masking model used in Experiment 3 is an 8-layer U-Net architecture as well. The masking model is trained to minimize loss, which may be calculated according to Equation 4 above. For the purposes of discussing Experiment 3, the masking model used in this experiment, and exemplifying an embodiment according to the present disclosure, will be referred to as the disclosed masking model (which generates the disclosed mask).

The performance of the disclosed mask generated by the disclosed masking model is compared to a mask produced by quantile regression (a quantile mask), in which the uncertainty is estimated by bounding the value of each pixel with a confidence interval and by using a calibration procedure to guarantee that the value is within the confidence interval, as described in Angelopoulous. Moreover, the performance of the disclosed mask is also compared to an optimal mask generated using an oracle model optimized using a true image and a reconstructed image.

FIG. 10 is a plot 1000 of the mask size compared to the size of the optimal mask for the disclosed mask 1002 and the quantile mask 1004. As shown, there is a higher correlation between the disclosed mask 1002 and the optimal mask than between the quantile mask 1004 and the optimal mask.

FIG. 11 is a plot 1100 of the mask size distribution for the optimal mask 1102, the disclosed mask 1104, and the quantile mask 1106. As illustrated, the disclosed mask 1104 has a relatively low distribution compared to the quantile mask 1106. Moreover, the distribution of the disclosed mask 1104 is also closer to the distribution of the optimal mask 1102 than the distribution of the quantile mask 1106 is to the optimal mask 1102.

Overall, the disclosed masking model generates a relatively high quality mask for a wide variety of image-to-image models, as demonstrated by Experiments 1, 2, and 3. The disclosed masking model generally generates masks similar to an optimal mask and are a higher quality than other masking techniques.

Methods

Figure 12:
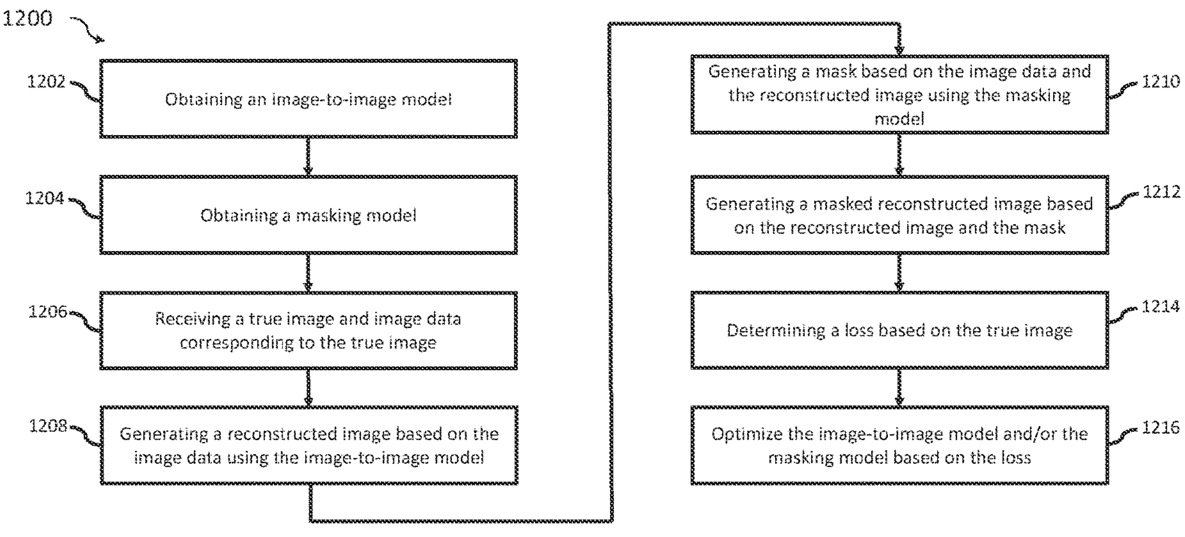
FIG. 12 is a flow chart illustrating an example method of training an image-to-image model and a masking model, according to one or more embodiments described herein.

FIG. 12 is a flowchart illustrating a method 1200 of training the image-to-image model 130 and the masking model 140, according to some embodiments of the present disclosure.

Step 1202 of the method 1200 may include obtaining an image-to-image model 130. The image-to-image model 130 may be any suitable model described herein. For example, the image-to-image model 130 may include a neural network.

Step 1204 may include obtaining a masking model 140. The masking model 140 may be any suitable model described herein. For example, the masking model 140 may include a neural network.

Step 1206 may include receiving a true image and image data 150 corresponding to the true image. The true image may represent the ideal or desired image that the image-to-image model 130 strives to reconstruct. For example, the true image may include complete and accurate image data and may include the desired color and resolution. The image data 150 may be collected from the true image, but may be incomplete, degraded, or inaccurate. For example, the image data 150 may be at a lower resolution, may be a gray-scale image, may have missing parts, or may be degraded. In some cases, the true image may have been compressed, altered, or degraded, which then may be input into the image-to-image model 130.

In some embodiments, the images received are biological or medical images. For example, the images may be collected from an endoscope during a colonoscopy procedure, from an MRI device, an x-ray device, or an ultrasound catheter any other suitable medical device for capturing medical images.

Step 1208 may include generating a reconstructed image 160 based on the image data 150 using the image-to-image model 130. The image-to-image model 130 may use any suitable process for generating the reconstructed image 160, as described herein. The reconstructed image 160 may be different than the true image.

Step 1210 may include generating a mask 170 based on the image data 150 and the reconstructed image 160 using the masking model 140. The masking model may use any suitable process for generating the mask 170, as described herein. The mask 170 may represent the uncertainty associated with the reconstructed image 160. For example, the masking model 140 may calculate an uncertainty value for each pixel in the reconstructed image 160. The masking model 140 may then generate a mask 170 based on the uncertainty value at each pixel of the image.

Step 1212 may include generating a masked reconstructed image 180 based on the reconstructed image 160 and the mask 170. The reconstructed image 160 and the mask 170 may be combined in any suitable way, as described herein. For example, the reconstructed image 160 and the mask 170 may be represented by vectors of the same size. The reconstructed image 160 vector may then be multiplied element-wise by the mask 170 vector. The resulting vector may correspond to the masked reconstructed image 180. The masked reconstructed image 180 may convey the uncertainty of the image at each part or pixel. For example, the mask 170 may mask part or all of the pixel of the reconstructed image 160 based on the uncertainty of the reconstructed image 160 at that pixel. Thus, the uncertainty associated with the masked reconstructed image 180 may be visually conveyed to a user.

Step 1214 may include determining a loss based on the true image. The loss may be calculated for each model 130, 140 individually or may be calculated for both models 130, 140. For example, the loss may be calculated for the image-to-image model 130 based on the true image. The image-to-image model 130 may be optimized in any suitable way including, for example, L1 loss, L2 loss, or SSIM. Moreover, the loss for the masking model 140 may also be calculated in any suitable way. For example, the loss may be calculated according to Equation 4 above. The loss in Equation 4 may be based on the true image.

Step 1216 may include optimizing the image-to-image model 130 and/or the masking model 140 based on the loss. The loss may be used to change or increment one or more values, scalars, parameters or user-defined variables within the neural network of the image-to-image model 130 and/or the masking model 140. The values may be changed to minimize the loss such that the reconstructed image 170 will approach the true image and the mask 170 will determine the most accurate uncertainty or, in some cases, may reflect the absolute error between the reconstructed image and the true image.

Figure 13:
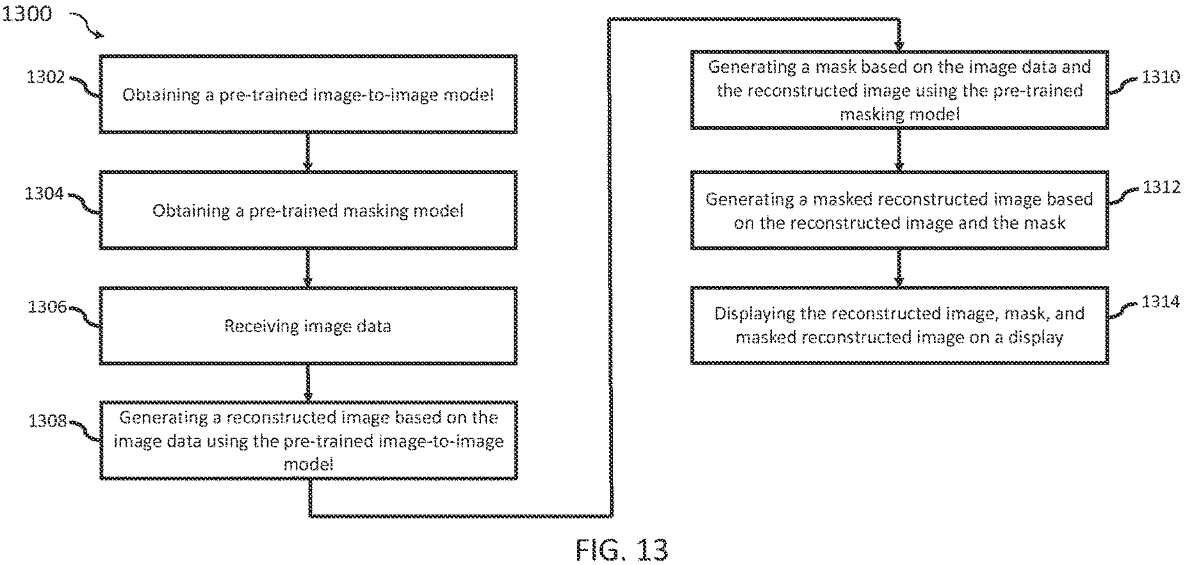
FIG. 13 is a flow chart illustrating an example method of using an image-to-image model and a masking model during the inference stage, according to one or more embodiments described herein.

FIG. 13 is a flowchart illustrating a method 1300 of generating a reconstructed image 160, mask 170, and masked reconstructed image 180 using the image-to-image model 130 and the masking model 140, according to some embodiments of the present disclosure. Method 1300 may be a method 1300 of using the models 130, 140 during the inference stage after the training stage (as described in FIG. 12 above).

Step 1302 of the method 1300 may include obtaining a pre-trained image-to-image model 130. The pre-trained image-to-image model 130 may be any suitable model described herein and may be trained according to method 1200 described in reference to FIG. 12 above. For example, the image-to-image model 130 may include a neural network that is trained using a true image and image data 150 corresponding to the true image.

Step 1304 may include obtaining a pre-trained masking model 140. The masking model 140 may be any suitable model described herein and may be trained according to the method 1200 described in reference to FIG. 12 above. For example, the masking model 140 may include a neural network that is trained using a true image, image data 150, and a reconstructed image 160.

Step 1306 may include receiving image data 150. The image data 150 may correspond to a true image. In some cases, the image data 150 may be collected from the true image, but may be incomplete, degraded, or inaccurate. For example, the image data 150 may be at a lower resolution, may be a gray-scale image, may have missing parts, or may be degraded. In some cases, the true image may have been compressed and the compressed image corresponds to the image data 150.

In some embodiments, the images received are biological or medical images. For example, the images may be collected from an endoscope during a colonoscopy procedure, from an MRI device, an x-ray device, or an ultrasound catheter any other suitable medical device for capturing medical images of a human being or animal.

Step 1308 may include generating a reconstructed image 160 based on the image data 150 using the pre-trained image-to-image model 130. The image-to-image model 130 may use any suitable process for generating the reconstructed image 160, as described herein. The reconstructed image 160 may be approximate or estimate the true image, but may be different than the true image.

Step 1310 may include generating a mask 170 based on the image data 150 and the reconstructed image 160 using the pre-trained masking model 140. The masking model may use any suitable process for generating the mask 170, as described herein. The mask 170 may represent the uncertainty associated with the reconstructed image 160. For example, the masking model 140 may calculate an uncertainty value for each pixel in the reconstructed image 160. The masking model 140 may then generate a mask 170 based on the uncertainty value at each pixel of the image.

Step 1312 may include generating a masked reconstructed image 180 based on the reconstructed image 160 and the mask 170. The reconstructed image 160 and the mask 170 may be combined in any suitable way, as described herein. For example, the reconstructed image 160 and the mask 170 may be represented by vectors of the same size. The reconstructed image 160 vector may then be multiplied element-wise by the mask 170 vector. The resulting vector may correspond to the masked reconstructed image 180. The masked reconstructed image 180 may convey the uncertainty of the image at each part or pixel. For example, the mask 170 may mask part or all of the pixel of the reconstructed image 160 based on the uncertainty of the reconstructed image 160 at that pixel. Thus, the uncertainty associated with the masked reconstructed image 180 may be visually conveyed to a user.

Step 1314 may include displaying the reconstructed image 160, the mask 170, and the masked reconstructed image 180 on a display 400, which may, for example, be the display 400 illustrated in FIG. 4. For example, the display 400 may include the reconstructed image 160, the mask 170, and the masked reconstructed image 180 side-by-side or in any other suitable arrangement. In some embodiments, one or more of the reconstructed image 160, the mask 170, and the masked reconstructed image 180 may not be displayed.

A number of variations are possible on the examples and embodiments described above. Accordingly, the logical operations making up the embodiments of the technology described herein are referred to variously as operations, steps, objects, elements, components, layers, modules, or otherwise. Furthermore, it should be understood that these may occur in any order, unless explicitly claimed otherwise or a specific order is inherently necessitated by the claim language.

Generally, any creation, storage, processing, and/or exchange of user data associated with the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In some embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

In several example embodiments, the elements and teachings of the various illustrative example embodiments may be combined in whole or in part in some or all of the illustrative example embodiments. In addition, one or more of the elements and teachings of the various illustrative example embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above. Connection references, such as "attached," "coupled," "connected," and "joined" are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

Additionally, the phrase "at least one of A and B" should be understood to mean "A, B, or both A and B." The phrase "one or more of the following: A, B, and C" should be understood to mean "A, B, C, A and B, B and C, A and C, or all three of A, B, and C." The phrase "one or more of A, B, and C" should be understood to mean "A, B, C, A and B, B and C, A and C, or all three of A, B, and C."

Although several example embodiments have been described in detail above, the embodiments described are examples only and are not limiting, and those skilled in the art will readily appreciate that many other modifications, changes, and/or substitutions are possible in the example embodiments without materially departing from the novel teachings and advantages of the present disclosure. Accordingly, all such modifications, changes, and/or substitutions are intended to be included within the scope of this disclosure as defined in the following claims.

What is claimed is:

1. A method of processing medical image data using a processor, the method comprising:

receiving image data representing a medical image;

generating a reconstructed image based on the image data;

generating a mask from the image data and the reconstructed image using a pre-trained machine learning model, wherein the mask comprises a plurality of pixels, each pixel of the plurality of pixels in the mask corresponding to a corresponding pixel of a plurality of pixels in the reconstructed image in a manner that the each pixel of the plurality of pixels in the mask has a corresponding uncertainty value selected from at least three uncertainty levels, the uncertainty value for the each pixel of the plurality of pixels in the mask being based on a distance between the corresponding pixel of the plurality of pixels in the reconstructed image and a corresponding pixel of the image data; and applying the mask to the reconstructed image to generate a masked reconstructed image.

2. The method of claim 1, wherein each of the at least three uncertainty levels is a value in a range of 0 to 1.

3. The method of claim 1, wherein generating the reconstructed image comprises colorization of the image data.

4. The method of claim 1, wherein generating the reconstructed image comprises identifying and estimating missing parts of the received image data.

5. The method of claim 1, wherein the image data represents an image of a first resolution, wherein the reconstructed image represents an image of a second resolution, and wherein the second resolution is higher than the first resolution.

6. The method of claim 1, wherein receiving the image data comprises collecting the image data from a medical device.

7. The method of claim 6, wherein the medical device is at least one of: an endoscope, a magnetic resonance imaging device, ultrasound device, and X-ray device.

8. The method of claim 1, wherein the pre-trained machine learning model is trained on a series of images to generate a mask for each image such that the distance between each masked reconstructed image and a corresponding true image is less than a first threshold with probability greater than a second threshold.

9. The method of claim 1, wherein the mask represents a visual representation of confidence that portions of the reconstructed image are accurate.

10. The method of claim 1, further comprising displaying the mask and the masked reconstructed image on a display.

11. A system for processing medical image data comprising:

an input interface configured to receive image data;

a memory configured to store a plurality of processor-executable instructions, the memory comprising:

an image-to-image model;

a masking model, wherein the masking model comprises a pre-trained machine learning model; and a processor configured to execute the plurality of processor-executable instructions to perform operations including:

receiving image data representing a medical image;

generating a reconstructed image based on the image data using the image-to-image model;

generating a mask from the image data and the reconstructed image using the masking model, wherein the mask comprises a plurality of pixels, each pixel of the plurality of pixels in the mask corresponding to a corresponding pixel of a plurality of pixels in the reconstructed image in a manner that the each pixel of the plurality of pixels in the mask has a corresponding uncertainty value selected from at least three uncertainty levels, the uncertainty value for the each pixel of the plurality of pixels in the mask being based on a distance between the corresponding pixel of the plurality of pixels in the reconstructed image and a corresponding pixel of the image data; and generating a masked reconstructed image based on the reconstructed image and the mask.

12. The system of claim 11, wherein each of the at least three uncertainty levels is a value in a range of 0 to 1.

13. The system of claim 11, wherein the pre-trained machine learning model is trained on a series of images to generate a mask for each image such that the distance between each masked reconstructed image and a corresponding true image is less than a first threshold with probability greater than a second threshold.

14. The system of claim 11, wherein the mask represents a visual representation of confidence that portions of the reconstructed image are accurate.

15. The system of claim 11, further comprising displaying the mask and the masked reconstructed image on a display.

16. A non-transitory processor-readable storage medium storing a plurality of processor-executable instructions for processing medical image data, the instructions being executed by a processor to perform operations comprising:

receiving image data representing at least one medical image;

generating a reconstructed image based on the image data;

generating a mask from the image data and the reconstructed image using a pre-trained machine learning model, wherein the mask comprises a plurality of pixels, each pixel of the plurality of pixels in the mask corresponding to a corresponding pixel of a plurality of pixels in the reconstructed image in a manner that the each pixel of the plurality of pixels in the mask has a corresponding uncertainty value selected from at least three uncertainty levels, the uncertainty value for the each pixel of the plurality of pixels in the mask being based on a distance between the corresponding pixel of the plurality of pixels in the reconstructed image and a corresponding pixel of the image data; and generating a masked reconstructed image based on the reconstructed image and the mask.

17. The non-transitory processor-readable storage medium of claim 16, wherein each of the at least three uncertainty levels is a value in a range of 0 to 1.

18. The non-transitory processor-readable storage medium of claim 16, wherein the pre-trained machine learning model is trained on a series of images to generate a mask for each image such that the distance between each masked reconstructed image and a corresponding true image is less than a first threshold with probability greater than a second threshold.

19. The non-transitory processor-readable storage medium of claim 16, wherein the mask represents a visual representation of confidence that portions of the reconstructed image are accurate.

20. The non-transitory processor-readable storage medium of claim 16, further comprising displaying the mask and the masked reconstructed image on a display.

* * * * *